United States Patent [19]

Urata et al.

[11] Patent Number: 5,623,078

[45] Date of Patent: Apr. 22, 1997

[54] PROCESS FOR PRODUCING AN INTERMEDIATE OF A NEW QUINOLONE COMPOUND

[75] Inventors: Yasuo Urata; Mamoru Fujita, both of Kanagawaken; Teruyo Sugiura, Chibaken; Fumitaka Ohizumi, Chibaken; Naoyuki Yoshida, Chibaken, all of Japan

[73] Assignee: Chisso Corporation, Osaka, Japan

[21] Appl. No.: 666,742

[22] Filed: Jun. 20, 1996

[30] Foreign Application Priority Data

Jun. 23, 1995 [JP] Japan ................... 7-180650

[51] Int. Cl.⁶ ............ C07D 209/02; C07D 209/52
[52] U.S. Cl. ........................................ 548/452
[58] Field of Search ............................ 548/452

[56] References Cited

U.S. PATENT DOCUMENTS 5,256,791  10/1993  Braish ...................... 548/452

FOREIGN PATENT DOCUMENTS 0010799  5/1980  European Pat. Off. .......... 209/52

*Primary Examiner*—Johann Richter
*Assistant Examiner*—Jane C. Oswecki
*Attorney, Agent, or Firm*—Leydig, Voit & Mayer

[57] ABSTRACT

A production process with good efficiency, and applicable to production of a synthetic intermediate of a new quinolone anti-fungus agent CP-99219, is provided.

A production process of an intermediate of a new quinolone compound expressed by the formula (IV)

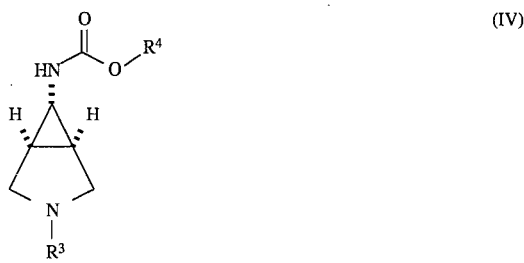

wherein $R^3$ represents a benzyl group, a diphenylmethyl group, etc. and $R^4$ represents a linear or branched alkyl group of 1 to 8C, a cycloalkyl group, etc.

which process employs as a starting substance, a cyclopropanetricarboxylic acid triester expressed by the formula (I)

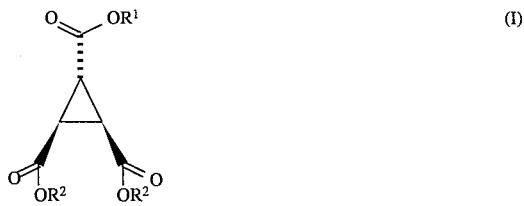

wherein $R^1$ and $R^2$ represent a linear or branched alkyl group, a cycloalkyl group, an aryl group or an aralkyl group, and passes through seven steps.

2 Claims, No Drawings

PROCESS FOR PRODUCING AN INTERMEDIATE OF A NEW QUINOLONE COMPOUND

BACKGROUND OF THE INVENTION

1. Field of Commercial Utilization

This invention relates to a process for producing an intermediate of a new quinolone compound useful as an intermediate of an anti-fungus agent, etc.

2. Description of the Related Art 7-(1a,5a,6a)-(6-Amino-3-azabicyclo[3,1,0]hexa-3-yl)-1-(2,4-difluorophenyl)-6-fluoro-1,4-dihydro-4-oxo-1,8-naphtylidine-3-carboxylic acid expressed by the formula (V)

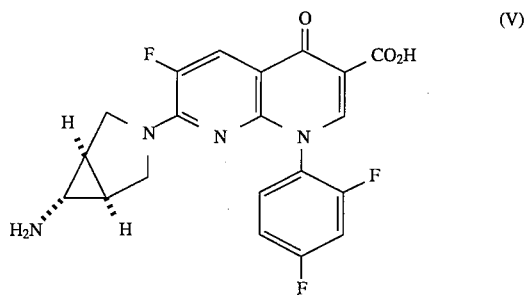

(Development No. CP-99,219 (U.S. Pat. No. 5,164,402 and U.S. Pat. No. 5,256,791), has a broad anti-fungus spector, and has been greatly expected as a new quinolone synthetic anti-fungus agent of the next generation.

As to the method of synthesizing an intermediate constituting the side chain of this compound, expressed by the formula (VI):

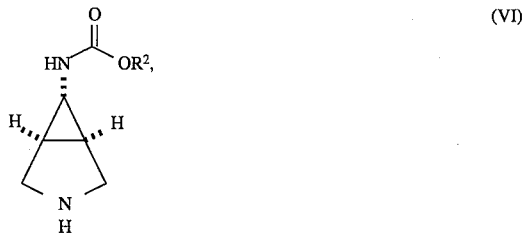

the following two representative preparation methods have been known:

the first method (1) is as follows:

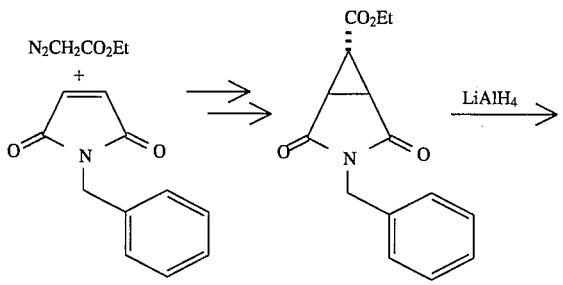

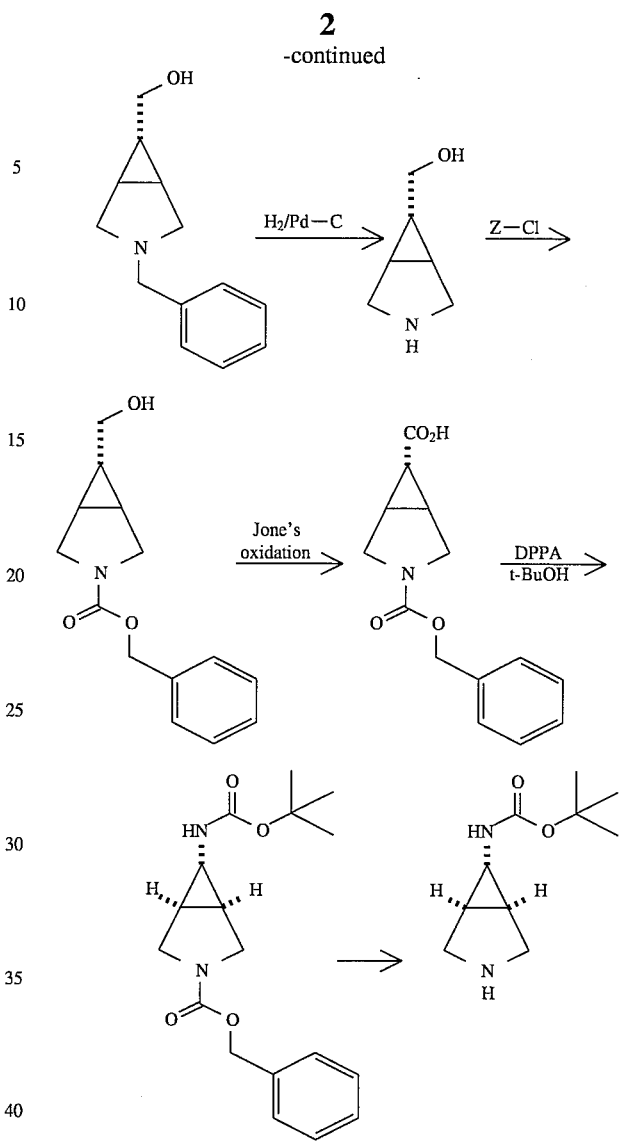

Z = benzyloxycarbonyl
DPPA = diphenylphosphorylazide

Namely, an azabicyclo ring is formed from ethyl diazoacetate and N-benzylmaleimide as starting materials, followed by reducing the carbonyl group with lithium aluminum hydride, changing the benzyl group to benzyloxycarbonyl group, oxidizing the hydroxyl group at the 6-position, to a carboxylic acid, further carrying out a Curtius rearrangement, and finally removing the protective group (U.S. Pat. No. 5,164,402).

The second method (2) is as follows:

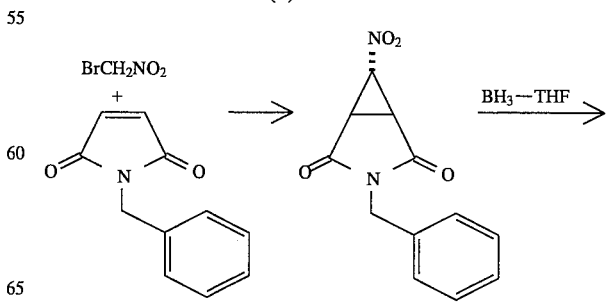

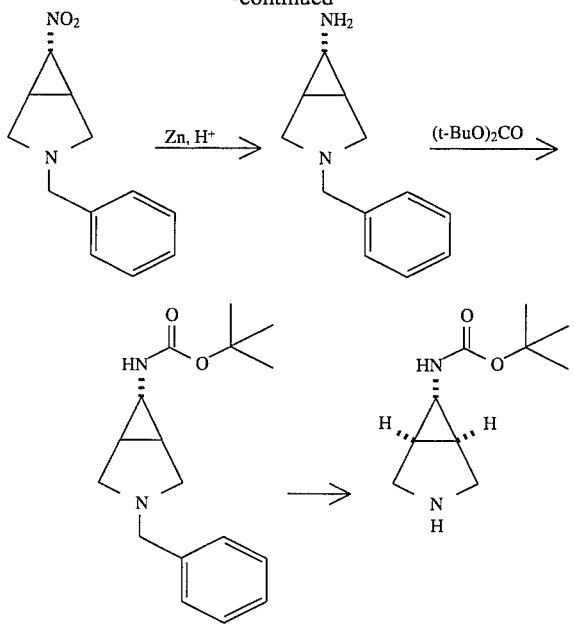

Namely, an azabicyclo ring core is formed from bromonitromethane and N-benzylmaleimide in the presence of a base, followed by reducing the carbonyl group with borane-THF, reacting the nitro group in the presence of zinc to convert it into an amino group, and finally protecting the amino group with a t-butyloxycarbonyl group (U.S. Pat. No. 5,256,791).

However, as to the method (1), ethyl diazoacetate which is highly explosive and limited in commercial availability, must be used as a starting material, and further, lithium aluminum hydride and Jone's reagent which are not easy to deal with in large quantities during the subsequent steps, are used, hence it is very difficult to commercially utilize the method.

Further, as to the method (2), although any of the steps subsequent to the formation of the azabicyclo ring have a high yield and a high efficiency; the efficiency of the ring formation from bromonitromethane and N-benzylmaleimide at the first step is as low as 17%; hence the efficiency through the total steps is reduced. Further, the bromonitromethane as the starting substance is explosive; hence its dealing is accompanied with difficulty. Namely, either of the methods could not have been regarded as a sufficient production process for obtaining the objective substance.

Problem to be Solved by the Invention

The present inventors have made extensive research related to these problems. As a result, we have found that when a cyclopropane tricarboxylic acid triester represented by the formula (I) as a starting substance is hydrolyzed, followed by dehydration condensation to obtain an acid anhydride (II), condensing this compound with an amine compound, to obtain a compound represented by the formula (III) as an intermediate, reducing its carbonyl group, to obtain an azide compound, and subjecting it to Curtius rearrangement, then an intermediate of a new quinolone compound represented by the formula (IV) can be obtained with a high yield. Thus, the present invention has been completed.

As apparent from the foregoing, the object of the present invention is to provide a process for producing a compound represented by the structural formula (IV) as a useful new quinolone compound intermediate.

SUMMARY OF THE INVENTION

The present invention relates to the following items (1) and (2):

(1) A process for producing an intermediate of a new quinolone compound expressed by the formula (IV)

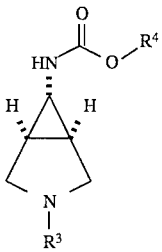

wherein $R^3$ represents a benzyl group, a diphenylmethyl group, a triphenylmethyl group, a benzyloxycarbonyl group, a diphenylmethyloxycarbonyl group or a triphenylmethyloxycarbonyl group and the substituents of the aromatic rings of these respective groups are selected from the group consisting of hydrogen, halogen groups of fluoro, chloro, bromo and iodo, a nitro group, a linear or branched alkyl group of 1 to 8 carbon atoms, a linear or branched alkoxy group of 1 to 8 carbon atoms, an amino group, and a linear or branched perfluoroalkyl group of 1 to 8 carbon atoms, and $R^4$ represents a linear or branched alkyl group of 1 to 8 carbon atoms, a cycloalkyl group, an aryl group or an aralkyl group, which process is characterized by subjecting a cyclopropanetricarboxylic acid triester expressed by the formula (I)

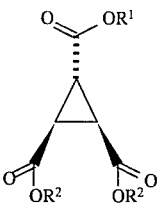

wherein $R^1$ and $R^2$ each represent a linear or branched alkyl group of 1 to 8 carbon atoms, a cycloalkyl group, an aryl group or an aralkyl group, as a starting substance, to hydrolysis and dehydration condensation, to prepare an acid anhydride expressed by the formula (II),

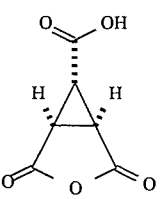

and condensing this acid anhydride with an amine compound, to obtain a compound expressed by the formula (III)

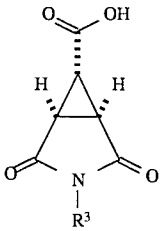

wherein $R^3$ has the same definition as described above, reducing the carbonyl group of this compound, preparing an azide compound in the presence of diphenylphosphorylazide (hereinafter abbreviated to DPPA) or a metal azide, subjecting this compound to Curtius rearrangement, to obtain a compound expressed by the formula (XV)

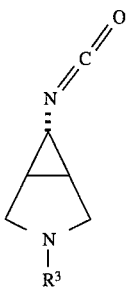

wherein $R^3$ has the same definition as described above, and reacting this compound with an alcohol.

(2) A process for producing an intermediate of a new quinolone compound according to item (1), wherein $R^3$ represents a benzyl group or a benzyloxycarbonyl group and $R^4$ represents a t-butyl group.

DETAILED DESCRIPTION OF THE INVENTION

The constitution and effectiveness of the present invention will be described below in details.

Namely, in the present invention, it is possible to obtain an intermediate of a new quinolone compound (IV), through the following synthesis route:

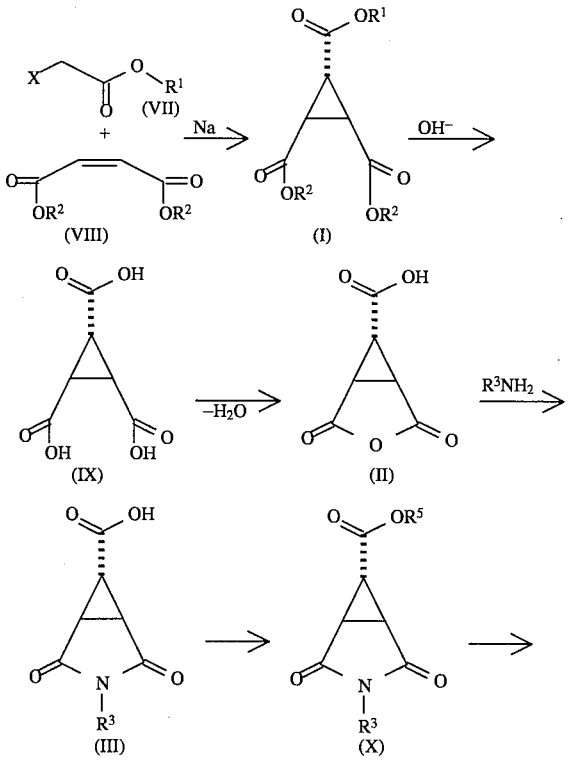

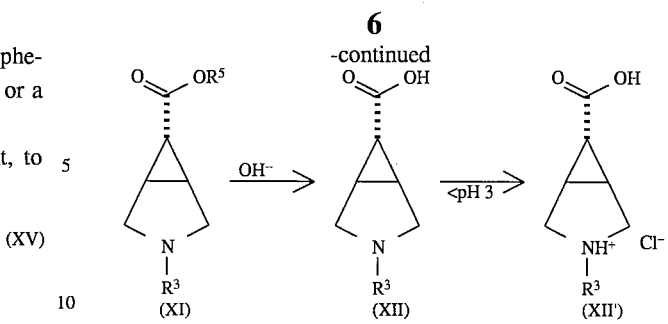

As the starting material, cyclopropanetricarboxylic acid triester expressed by the formula (I) is used. This ester is obtained for example by reacting a monohalogenoacetic acid ester (VII) (wherein $R^1$ represents a linear or branched alkyl group of 1 to 8 carbon atoms, a cycloalkyl group, an aryl group or an aralkyl group), with a maleic acid ester or a fumaric acid ester (VIII) (wherein $R^2$ represents a linear or branched alkyl group of 1 to 8 carbon atoms, a cycloalkyl group, an aryl group or an aralkyl group) in the presence of a metallic sodium, as disclosed in Japanese patent application laid-open No. Sho 53-73542.

Next, when the triester (I) is hydrolyzed in the presence of a general base such as NaOH, LiOH or KOH, it is possible to easily obtain a cyclopropanetricarboxylic acid (IX).

In more detail, the tricarboxylic acid triester expressed by the formula (I) is obtained by reacting a dicarboxylic acid diester expressed by the formula (VIII) with a monohalogenated acetic acid ester expressed by the formula (VII) in the presence of metallic sodium, to form a three-membered ring. As an example of the dicarboxylic acid diester used in the reaction, maleic acid esters and fumaric acid esters are mentioned.

As the examples of the maleic acid esters and the fumaric acid esters, dimethyl maleate, diethyl maleate, dipropyl maleate, diisopropyl maleate, dibutyl maleate, dicyclohexyl maleate, diphenyl maleate, dibenzyl maleate, dimethyl fumarate, diethyl fumarate, dipropyl fumarate, diisopropyl fumarate, dibutyl fumarate, dicyclohexyl fumarate, diphenyl fumarate, dibenzyl fumarate, etc. are mentioned.

As the examples of the monohalogenic acid esters, chloroacetic acid esters and bromoacetic acid esters are mentioned. As the exmaples of chloroacetic acid esters and the bromoacetic acid esters, methyl chloroacetate, ethyl chloroacetate, propyl chloroacetate, isopropyl chloroacetate, butyl chloroacetate, cyclohexyl chloroacetate, phenyl chloroacetate, benzyl chloroacetate, methyl bromoacetate, ethyl bromoacetate, propyl bromoacetate, isopropyl bromoacetate, butyl bromoacetate, cyclohexyl bromoacetate, phenyl bromoacetate, benzyl bromoacetate, etc. are mentioned.

As to the metallic sodium used in the present invention, any form may be used such as small pieces prepared from commercially available rod form or spherical form thereof, or a dispersion of sodium having a particle diameter of 1 mm or less. As the reaction solvent, any of inert solvents may be used, and among them aromatic hydrocarbon solvents such as benzene, toluene, xylene, etc. are preferably used. As to the reaction temperature, 50° to 150° C. is suitable, and 60° to 130° C. is particularly preferred.

As to the tricarboxylic acid triesters expressed by the formula (I), there are geometrical isomers of cis form and trans form, based upon the steric structure of ester groups, but according to the present reaction, it is possible to mainly obtain trans isomers.

The tricarboxylic acid expressed by the formula (IX) can be obtained by hydrolyzing the tricarboxylic acid triesters expressed by formula (I) under basic conditions. As to the examples of bases used in the reaction, lithium hydroxide, sodium hydroxide, potassium hydroxide, barium oxide, etc. are mentioned. As to the reaction solvent, alcoholic solvents such as methanol, ethanol or mixed solvents of these solvents with water are used. As to the reaction temperature, −20° to 150° C. are suitable, and 0° to 100° C. are particularly preferred.

The acid anhydride expressed by the formula (II) is obtained by thermally dehydrating the tricarboxylic acid expressed by the formula (IX). This reaction proceeds even without any solvent, but in order to advance the reaction more smoothly, it is preferred to carry out the reaction in the presence of an acid anhydride of a lower fatty acid such as acetic anhydride, or an acid chloride such as acetyl chloride. As to the reaction temperature, 50° to 200° C. is suitable, and 100° to 150° C. is particularly preferred.

The acid imide expressed by the formula (III) can be obtained according to two step reactions, that is, by reacting the acid anhydride expressed by the formula (II) with a primary amine to form a dicarboxylic acid monoamide, followed by thermally dehydrating the monoamide. This reaction proceeds even in the absence of any solvent, but when it is heated in acetic anhydride in the presence of sodium acetate, the reaction can be easily advanced. As to the reaction temperature, 50° to 200° C. is suitable, and 100° to 150° C. is particularly preferred.

The carboxylic acid ester expressed by the formula (X) can be obtained by heating the acid imide expressed by the formula (III) in the presence of an acid catalyst in an alcohol. As the examples of the alcohol, methanol, ethanol, propanol, isopropanol, butanol, etc. can be mentioned. It is possible to obtain a methyl ester, an ethyl ester, a propyl ester, an isopropyl ester, a butyl ester, etc. corresponding to the kinds of alcohols used.

As the examples of the acid for the catalyst, inorganic acids such as hydrogen chloride, sulfuric acid, etc. and organic acids such as camphor sulfonic acid, etc. are mentioned. The reaction temperature is suitable to be 30° to 150° C., and particularly preferable to be 50° to 100° C.

The compound expressed by the formula (XI) can be obtained by selectively reducing the carbonyl groups of the carboxylic acid ester expressed by the formula (X). In this reaction, the carboxylic acid ester is not reduced. As examples of the reducing agent used in this reaction, diborane, borane-tetrahydrofuran complex, borane-dimethylsulfide complex, etc., can be mentioned.

As these agents, commercially available agents may be used, but it does not matter if diborane generated from sodium borohydride-boron trifluoride-ether complex is used in this reaction. As the reaction solvent, any inert solvent can be used, but ether solvents such as diethyl ether, tetrahydrofuran, dioxane, etc. are preferably used. The reaction temperature is suitable to be −30° to 100° C., and particularly preferable to be −10° to 80° C.

The carboxylic acid derivative expressed by the formula (XII) can be obtained by hydrolyzing the compound expressed by the formula (XI) under basic conditions. As examples of the base used in the present invention, lithium hydroxide, sodium hydroxide, potassium hydroxide, barium hydroxide, etc. are mentioned. As the reaction solvent, alcoholic solvents such as methanol, ethanol or mixed solvents thereof with water are used.

The reaction temperature is suitably 0° to 100° C., particularly preferably 0° to 50° C.

In addition, at the time of completion of the reaction, it is necessary to add an acid for neutralization, and a free tertiary amine (the carboxylic acid expressed by the formula (XII)) is obtained in the vicinity of pH 7, and a hydrochloride is obtained at pH 3 or lower.

In the carboxylic acid expressed by the formula (XII) or its hydrochloride (XII'), compounds where $R^3$ is a benzyloxycarbonyl group, a diphenylmethyloxycarbonyl group or triphenylmethyloxycarbonyl group, can be prepared from the compound expressed by the formula (XI), according to the following reaction equations:

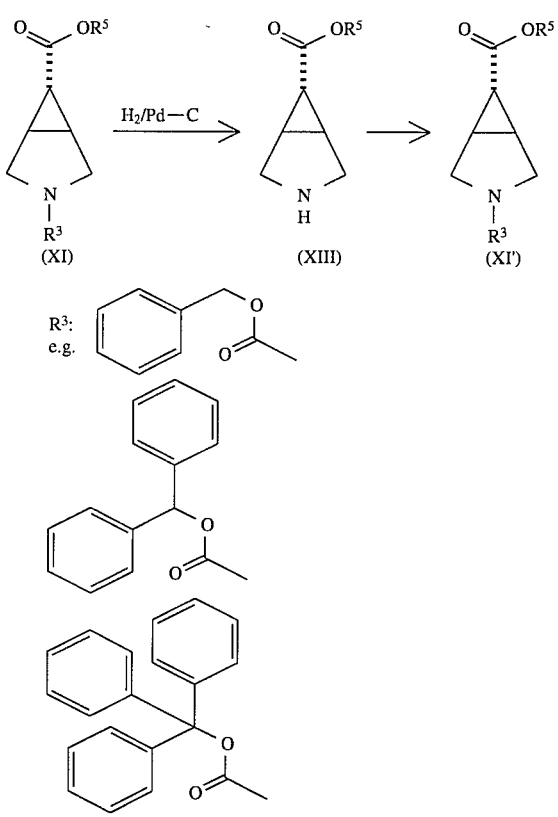

In the above equations, $R^3$ of the formula (XI) represents a benzyl group, a diphenylmethyl group or a triphenylmethyl group, and $R^3$ of the compound (XI') represents a benzyloxycarbonyl group, a diphenylmethyloxycarbonyl group or a triphenylmethyloxycarbonyl group. The substituents of the aromatic rings of these groups are selected from among hydrogen, halogen groups of fluoro, chloro, bromo and iodo, a nitro group, linear or branched alkyl groups of 1 to 8 carbon atoms, linear or branched alkoxy groups of 1 to 8 carbon atoms, amino group, and linear or branched perfluoroalkyl groups of 1 to 8 carbon atoms. $R^5$ represents linear or branched alkyl groups of 1 to 8 carbon atoms, a cycloalkyl group, a aryl group or a aralkyl group.

Namely, the amine compound expressed by the formula (XIII) is obtained by hydrolyzing the substituent of the amino group in the compound expressed by the formula (XI) in the presence of a catalyst. As the catalyst used for the reaction, palladium-carbon, palladium hydroxide-carbon, Raney Ni, etc. are mentioned.

As the reaction solvent, any inert solvent may be used, and preferably, alcoholic solvents such as methanol, ethanol, or mixed solvent thereof with water are used.

The reaction temperature is suitable to be 0° to 100° C. and particularly preferable to be 0° to 50° C. The hydrogen pressure in the reaction is suitable to be 1 to 10 atm, and particularly preferred to be 1 to 5 atm. Further, the carboxylic acid derivative expressed by the formula (XI') can be obtained by carbamoylizing the amine compound expressed by the formula (XIII) according to a conventional method. As a concrete method for converting it into a carbamate, a method of reacting a chloroformic acid ester in the presence of an amine is exemplified.

More concretely, for example, in order to obtain a benzyl carbamate, it may be reacted with benzyl chloroformate in the presence of triethylamine. As the reaction solvent, any of halogenated hydrocarbon solvents such as methylene chloride, chloroform, etc., and ether system solvents such as diethyl ether, tetrahydrofuran, etc. may be used. The reaction temperature is suitable to be −20° to 100° C., and particularly preferred to be 0° to 50° C.

It is possible to obtain the carboxylic acid or its hydrochloride expressed by formula (XII) or (XII'), also from the compound expressed by the formula (XI'), by hydrolyzing under a basic condition. As the examples of bases used in the reaction, lithium hydroxide, sodium hydroxide, potassium hydroxide, barium hydroxide, etc. are mentioned.

As the reaction solvent, alcoholic solvents such as methanol, ethanol or mixtures thereof with water are preferably used. The reaction temperature is suitable to be 020 to 100° C., and particularly preferred to be 0° to 50° C.

Using the carboxylic acid or its hydrochloride expressed by the formula (XII) or (XII') as a starting raw material, and carrying out a Curtius rearrangement according to the following reaction equations, it is possible to prepare a carbamate expressed by the formula (IV) and an amine compound expressed by the formula (XVI):

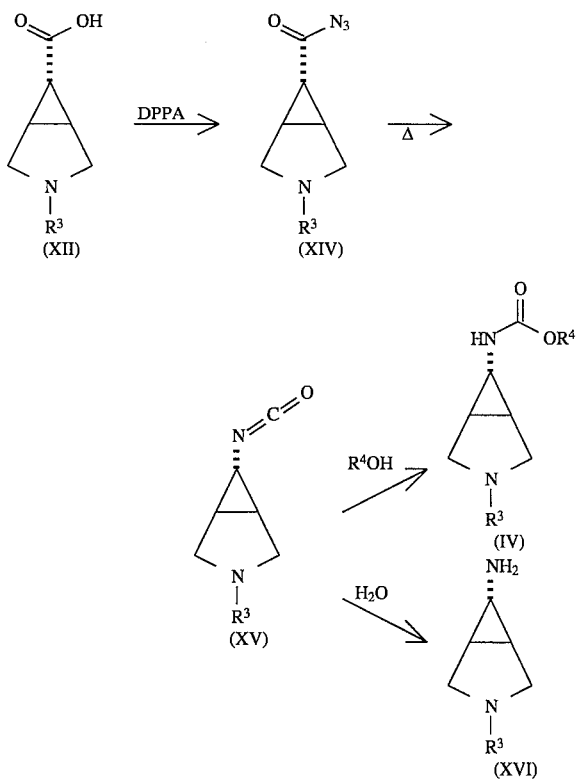

In the above equations, $R^3$ represents a benzyl group, a diphenylmethyl group, a triphenylmethyl group, a benzyloxycarbonyl group, a diphenylmethyloxycarbonyl group or triphenylmethyloxycarbonyl group. The substituents of the aromatic rings of these groups are selected from among hydrogen, halogen groups of fluoro, chloro, bromo and iodo, nitro group, a linear or branched alkyl group of 1 to 8 carbon atoms, a linear or branched alkoxy group of 1 to 8 carbon atoms, an amino group and a linear or branched perfluoroalkyl group. $R^4$ represents a linear or branched alkyl group of 1 to 8 carbon atoms, a cycloalkyl group, an aryl group or an aralkyl group.

The hydrochloride of the carboxylic acid expressed by the formula (XII') may be used as it is, for the reaction, but it is more preferable to remove the salt formed by adding the base, by means of filtration operation. As examples of the base added, any of bases capable of forming a salt with hydrochloric acid may be used, but organic bases such as triethylamine, pyridine, etc. and inorganic bases such as sodium carbonate, potassium carbonate, sodium hydroxide, potassium hydroxide, etc. are preferably used.

When the carboxylic acid expressed by the formula (XII) is reacted with diphenylphosphoryl azide (DPPA), it is converted into an acylazide (XIV), and when this acyl azide is heated in a solvent, it is easily thermally transformed into the isocyanate (XV). The quantity of DPPA used is calculated to be necessary to be one time mol or more that of the carboxylic acid, but preferably 1 to 3 times mols are used. As the examples of the reaction solvent, any inert solvents may be used, but aromatic hydrocarbon solvents such as benzene, toluene, xylene, etc. are preferably used.

The reaction temperature is suitable to be 50° to 0° C., particularly preferred to be 70° to 150° C. When this isocyanate (XV) is heated in an alcohol, it is possible to obtain the carbamate expressed by the formula (IV).

As examples of the alcohol used for the reaction, methanol, ethanol, propanol, isopropanol, butanol, t-butanol, etc. are mentioned, and depending upon the kinds of the alcohols used, it is possible to obtain the corresponding methyl carbamate, ethyl carbamate, propyl carbamate, isopropyl carbamate, butyl carbamate, t-butyl carbamate, etc.

The quantity of the alcohol used is calculated to be necessary to be one time mol or more, that of the carboxylic acid, but it is usually used in a large excess. When water is used in place of the alcohol, it is possible to obtain an amine compound expressed by the formula (XVI).

By the above procedure, it is possible to produce an intermediate of a new quinolone compound.

Further, the Curtius rearrangement can be also carried out by using a metal azide. The carboxylic acid expressed by the formula (XII) or its hydrochloride is converted into a mixed acid anhydride or an acid chloride according to a conventional manner, followed by reacting either of them with a metal azide, to obtain the acylazide expressed by the formula (XIV). As a concrete method of converting them into the mixed acid anhydride, a method of reacting a chloroformic acid ester in the presence of an amine is exemplified.

As examples of the amine used herein, trimethylamine, triethylamine, pyridine, collidine, etc. are mentioned, and as examples of chloroformic acid ester, methyl chloroformate, ethyl chloroformate, etc. are mentioned. Further, as a concrete method of converting into an acid chloride, a method of reacting thionyl chloride, phosphoryl chloride, phosphorus pentachloride, phosphorus trichloride, etc. is exemplified.

As examples of the metal azide used for the reaction, lithium azide, sodium azide, etc. are mentioned. The quantity of the metal azide used is calculated to be necessary to be one time mol or more the quantity of the carboxylic acid, but 1 to 3 times mols are preferably used. As the reaction solvent, a mixed solvent of a solvent miscible with water, such as acetone, dioxane, alcohol, etc. is preferably used. The reaction temperature is suitable to be −20° to 100° C., and is particularly preferred to be 0° C. to room temperature.

The thus obtained acyl azide is converted into the carbamate expressed by the formula (IV) via the isocyanate expressed by the formula (XV), in the same manner as above. As examples of the alcohol used for the reaction, methanol, ethanol, propanol, isopropanol, butanol, t-butanol, etc. are mentioned, and depending upon the kinds of alcohols used, it is possible to obtain the corresponding methyl carbamate, ethyl carbamate, propyl carbamate, isopropyl carbamate, butyl carbamate, t-butyl carbamate, etc. The quantity of the alcohol used is calculated to be one time mol or more that of the carboxylic acid, but a large excess is usually used. When water is used in place of alcohol, an amine compound expressed by the formula (XVI) is obtained.

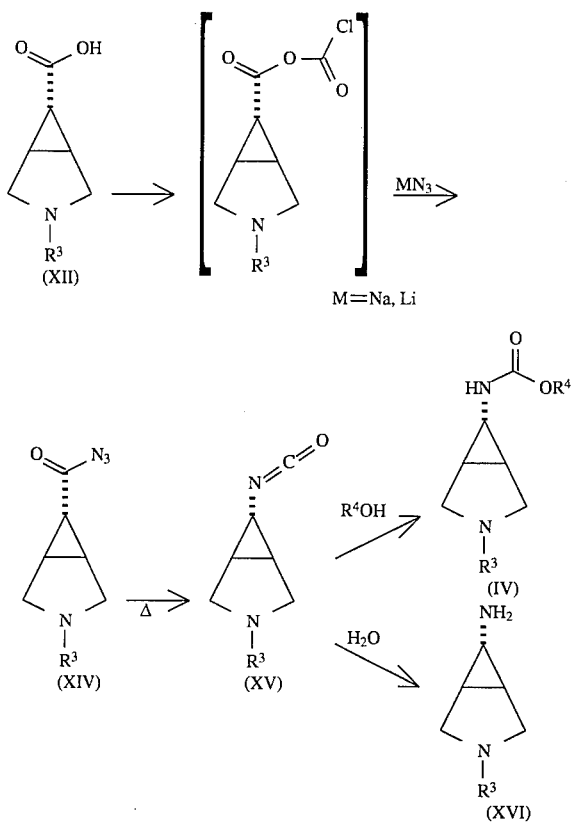

EXAMPLE

The present invention will be described in more detail by way of Reference example, Example and Comparative example. In addition, the present invention should not be construed to be limited thereto.

Reference Example

Preparation of trimethyl cyclopropane-1,2,3-tricarboxylate

A metallic sodium dispersion (about 40% by weight) (67.3 g, 1.17 mol) in liquid paraffin was added to toluene (700 ml) and the mixture was heated to 65° C., followed by dropwise adding a mixed solution of dimethyl maleate (145.1 g, 1.01 mol) with methyl monochloroacetate (163.5 g, 1.51 mol) so as to keep 65° to 70° C., thereafter heating the mixture at the same temperature with stirring for 4 hours, cooling the reaction mixture, slowly dropwise adding methanol (33 ml), further adding water, separating an organic layer, extracting the aqueous layer with ethyl acetate, combining the resulting organic layers, drying the mixture over anhydrous magnesium sulfate, and concentrating the organic layer under reduced pressure and purifying the residue (150.9 g) by distillation, to obtain methyl cyclopropane-1,2,3-carboxylate (84.5 g, 391 mmol, 39%).

1H-NMR (CDCl$_3$):δ2.50–2.90(m, 3H), 3.72 (s, 6H), 3.74 (s, 3H)

Example 1

Step 1:Preparation of cyclopropane-1,2,3-tricarboxylic acid

Trimethyl cyclopropane-1,2,3-tricarboxylate (20.6 g, 95.2 mmols) was dissolved in methanol (200 ml), followed by dropwise adding sodium hydroxide (23.7 g, 593 mmol) (dissolved in water (100 ml)) at room temperature, thereafter heating and reacting the mixture under reflux for one hour, cooling the reaction product, adding conc. hydrochloric acid (40 g, 1.1 mol), concentrating the reaction solution, adding acetone (200 ml) to the concentrated residue, heating the mixture under reflux for 2 hours, filtering off the precipitate, and concentrating the filtrate under reduced pressure, to obtain cyclopropane-1,2,3-tricarboxylic acid (16.0 g, 91.9 mmol, 97%).

1H-NMR (DMSO-d$_6$-CDCl$_3$):δ2.30–2.80 (m, 3H)

Step 2:Preparation of 2,4-dioxo-3-oxabicyclo-[3.1.0]hexane-6-carboxylic acid

Acetic acid (58.8 ml, 933 mmol) and acetic anhydride (20.4 ml, 185 mmol) were added to cyclopropane-1,2,3-tricarboxylic acid (24.4 g, 140 mmol), followed by reacting the mixture while heating under reflux for 2 hours, concentrating the reaction solution into a half volume, filtering off deposited crystals, washing them with heptane and drying under reduced pressure, to obtain 2,4-dioxo-3-oxabicyclo [3.1.0]hexane-6-carboxylic acid (18.1 g, 116 mmol, 83%).

1H-NMR (DMSO-d$_6$-CDCl$_3$):δ2.64(t,J=2.9 Hz, 1H), 3.14 (d, J=2.9 Hz, 2H)

Step 3: Preparation of 3-benzyl-2,4-dioxo-3-azabicyclo [3.1.0]hexane-6-carboxylic acid 2,4-Dioxo-3-oxabicyclo[3.1.0]hexane-6-carboxylic acid (11.2 g, 71.8 mmol) was dissolved in acetone (60 ml), followed by successively dropwise adding triethylamine (9.9 ml, 71.8 mmol) and benzylamine (9.4 ml, 86.1 mmol), agitating the mixture at room temperature for 3 hours, concentrating the reaction solution, adding sodium acetate (3.53 g, 43.1 mmol) and acetic anhydride (32.6 ml, 344 mmol) to the resulting concentrated residue and heating the mixture under reflux for one hour.

The reaction solution was concentrated, followed by dissolving the concentrated residue in water, adding conc. hydrochloric acid till its pH reached 2, to deposit crystals, filtering off the crystals, washing them with toluene and heptane, drying under reduced pressure, to obtain 3-benzyl-2,4-dioxo-3-azabicyclo[3.1.0]hexane-6-carboxylic acid (15.0 g, 61.2 mmol, 85%), and recrystallizing it from ethyl acetate to obtain a pure product.

1H-NMR (CD$_3$OD):δ2.33(t, J=2.9 Hz, 1H), 2.89(d, J=2.9 Hz, 2H), 4.49 (s, 2H), 7.28 (s, 5H)

Step 4:Preparation of ethyl 3-benzyl-2,4-dioxo-3-azabicyclo[3.1.0]hexane-6-carboxylate 3-Benzyl-2,4-dioxo-3-azabicyclo[3.1.0]hexane-6-carboxylic acid (1.50 g, 6.13 mmol) was suspended in ethanol (30 ml), followed by adding p-toluenesulfonic acid monohydrate (145 mg, 0.76 mmol), heating the mixture under reflux for 8 hours, adding sodium carbonate to the reaction solution for neutralization, concentrating the mixture under reduced pressure, adding a saturated aqueous sodium bicarbonate to the reaction residue, extracting it with ethyl acetate, washing the extraction solution successively with water and saturated aqueous NaCl solution, drying it over anhydrous magnesium sulfate, concentrating the resulting solution to obtain ethyl 3-benzyl-2,4-dioxo-3-azabicyclo

[3.1.0]hexane-6-carboxylate (1.51 g, 5.52 mmol, 90%), and recrystallizing it from ethanol to obtain a pure product.

1H-NMR (CDCl$_3$):δ1.18 (t, 7.2 Hz, 3H), 2.20 (t, J=2.9 Hz, 1H), 2.78 (d, J=2.9 Hz, 2H), 4.10 (q, 7.2 Hz, 2H), 4.42 (s, 2H), 7.21 (s, 5H)

Step 5:Preparation of ethyl 3-benzyl-3-azabicyclo[3.1.0] hexane-6-carboxylate

Ethyl 3-benzyl-2,4-dioxo-3-azacyclo[3.1.0]hexane-6-carboxylate (1.51 g, 5.52 mmol) was dissolved in tetrahydrofuran (30 ml), followed by dropwise adding boranetetrahydrofuran complex (1M-tetrahydrofuran solution) (22 ml) under ice cooling, agitating the mixture at the same temperature for 3.5 hours, adding ethanol (15 ml) to the reaction solution, heating the mixture under reflux for one hour and concentrating the solution under reduced pressure.

Water was added to the concentrated residue, followed by extracting the mixture with ethyl acetate, washing the extraction solution successively with water and saturated aqueous NaCl solution, drying over anhydrous magnesium sulfate, concentrating the solution, and purifying the residue (1.35 g) according to column chromatography (heptane: ethyl acetate=4:1), to obtain ethyl 3-benzyl-3-azabicyclo [3.1.0]hexane-6-carboxylate (1.11g, 4.53 mmol, 82%).

1H-NMR (CDCl$_3$):δ1.25 (t, 7.2 Hz, 3H), 1.85–2.05 (m, 2H), 2.00–2.20 (m, 1H), 2.40 (d, J=9.0 Hz, 2H), 3.02 (d, J=9.0 Hz, 2H), 3.58 (s, 2H), 4.10 (q, J=7.2 Hz, 2H), 7.25 (s, 5H)

Step 6:Preparation of 3-benzyl-3-azabicyclo[3.1.0]-hexane-6-carboxylic acid hydrochloride Sodium hydroxide (0.99 g, dissolved in water (5.7 ml)) was dropwise added to a mixture of ethyl 3-benzyl-3-azabicyclo[3.1.0]hexane-6-carboxylate (3.06 g, 12.5 mmol), methanol (18 ml) and water (6 ml), under ice cooling, followed by agitating the mixture at the same temperature for one hour and further at room temperature for 5.5 hours, concentrating the reaction solution to ⅓–¼ quantity, adding 4M hydrochloric acid till the pH became 2, to deposit crystals, filtering off the crystals, and drying them under reduced pressure, to obtain 3-benzyl-3-azabicyclo[3.1.0]-hexane-6-carboxylic acid hydrochloride (3.07 g, 12.1 mmol, 97%).

1H-NMR (CD$_3$CD):δ2.33 (s, 3H), 3.62 (s, 4H), 4.39 (s, 2H), 7.30–7.80 (m, 2H)

Step 7:Preparation of 3-benzyl-6-t-butoxycarbonylamino-3-azabicyclo[3.1.0]hexane A mixture of 3-benzyl-3-azabicyclo[3.1.0]hexane-6-carboxylic acid hydrochloride (101 mg, 0.40 mmol), triethylamine (185 mg, 1.83 mmol), DPPA (180 mg, 0.65 mmol), t-butanol (4 ml) and toluene (3 ml) was heated under reflux in a nitrogen atmosphere for 23 hours, followed by cooling the reaction mixture, pouring it into water, extracting with toluene, washing the organic layer successively with an aqueous solution of sodium carbonate, water and a saturated aqueous NaCl solution, drying over anhydrous magnesium sulfate, distilling off the solvent under reduced pressure, and purifying the residue according to thin-layer chromatography (developing solvent: chloroform:methanol=20:1), to obtain 3-benzyl-6-t-butoxycarbonylamino-3-azabicyclo [3.1.0]hexane (27 mg, 0.09 mmol, 24%).

Example 2

A mixture of 3-benzyl-3-azabicyclo[3.1.0]hexane-6-carboxylic acid (116 mg, 0.53 mmol) obtained by treating ethyl 3-benzyl-3-azabicyclo[3.1.0]hexane-6-carboxylate obtained in step 5 of Example 1, with an aqueous solution of NaOH, with triethylamine (239 mg, 2.36 mmol), DPPA (303 mg, 1.10 mmol) and t-butanol (4 ml), was heated under reflux in a nitrogen atmosphere for 19 hours, followed by cooling the reaction mixture, pouring it into water, extracting with toluene, washing the organic layer successively with an aqueous solution of Na$_2$CO$_3$, water and a saturated aqueous solution of NaCl, drying over anhydrous magnesium sulfate, distilling off the solvent under reduced pressure and purifying the residue according to thin-layer chromatography (developing solvent: chloroform:methanol=20:1), to obtain 3-benzyl-6-t-butoxycarbonylamino-3-azabicyclo[3.1.0]hexane (47 mg, 0.16 mmol, 31%).

Effectiveness of the Invention

According to the present invention, a process for producing an intermediate of a new quinolone compound was improved to a large extent and with good efficiency. Concretely, according to a production process disclosed in U.S. Pat. No. 5,256,791, 3-benzyloxycarbonyl-6-t-butoxycarbonylamino-3-azabicyclo[3.1.0]hexane was obtained in a total yield of 10.7%, using N-benzyl maleimide as a starting substance. On the other hand, according to the present invention, 3-benzyl-6-t-butoxycarbonylamino-3-azabicyclo [3.1.0]hexane was obtained from cyclopropanetricarboxylic acid in a total yield of 12.1%; thus, the yield was improved as compared with a conventional process.

The compound obtained according to the process of the present invention is very useful as a synthetic intermediate of 7-(1a,5a,6a)-(6-amino-3-azabicyclo[3.1.0]-hexa-3-yl)-1-(2,4-difluorophenyl)-6-fluoro-1,4-dihydro-4-oxo-1,8-naphthylidine-3-carboxylic acid (CP-99219) which is a new quinolone anti-fungus agent.

What we claim is:

1. A process for producing an intermediate of a new quinolone compound expressed by the formula (IV)

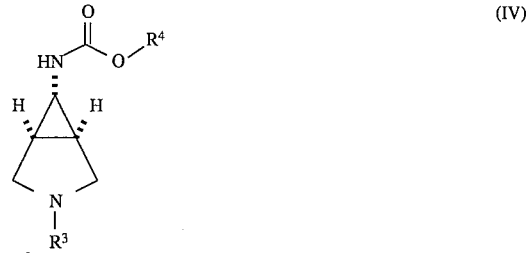

wherein R$^3$ represents a benzyl group, a diphenylmethyl group, a triphenylmethyl group, a benzyloxycarbonyl group, a diphenylmethyloxycarbonyl group or a triphenylmethyloxycarbonyl group and the substituents of the aromatic rings of these respective groups are selected from the group consisting of hydrogen, halogen groups of fluoro, chloro, bromo and iodo, a nitro group, a linear or branched alkyl group of 1 to 8 carbon atoms, a linear or branched alkoxy group of 1 to 8 carbon atoms, an amino group, and a linear or branched perfluoroalkyl group of 1 to 8 carbon atoms, and R$^4$ represents a linear or branched alkyl group of 1 to 8 carbon atoms, a cycloalkyl group, an aryl group or an aralkyl group, which process comprises subjecting a cyclopropanetricarboxylic acid triester expressed by the formula (I)

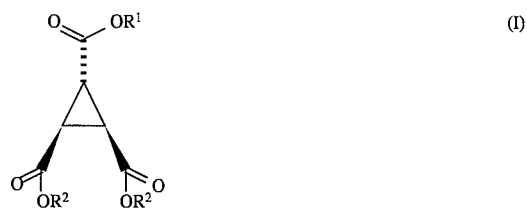

wherein R$^1$ and R$^2$ each represent a linear or branched alkyl group of 1 to 8 carbon atoms, a cycloalkyl group, an aryl group or an aralkyl group, as a starting substance, to hydrolysis and dehydration condensation, to prepare an acid anhydride expressed by the formula (II),

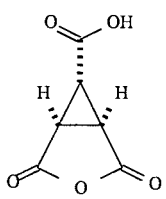
(II)

and condensing this acid anhydride with an amine compound, to obtain a compound expressed by the formula (III)

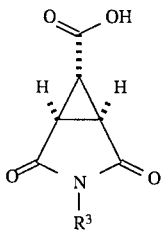
(III)

wherein $R^3$ has the same definition as described above, reducing the carbonyl group of the formula III compound, reacting a metal azide or diphenylphosphorylazide with the Formula III reduced carbonly compound, subjecting this compound to Curtius rearrangement, to obtain a compound expressed by the formula (XV)

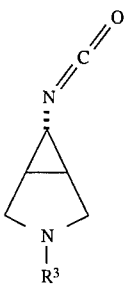
(XV)

wherein $R^3$ has the same definition as described above, and reacting this compound with an alcohol.

2. A process for producing an intermediate of a new quinolone compound according to claim 1, wherein $R^3$ represents a benzyl group or benzyloxycarbonyl group and $R^4$ represents a t-butyl group.

* * * * *